United States Patent
Jacobs

(10) Patent No.: US 6,838,104 B2
(45) Date of Patent: Jan. 4, 2005

(54) PROCESS FOR THE PRODUCTION OF TOCOTRIENOLS

(75) Inventor: Lewis Jacobs, Decatur, IL (US)

(73) Assignee: Archer Daniels Midland Company, Decatur, IL (US)

(*) Notice: Subject to any disclaimer, the term of this patent is extended or adjusted under 35 U.S.C. 154(b) by 423 days.

(21) Appl. No.: 10/012,047

(22) Filed: Dec. 11, 2001

(65) Prior Publication Data

US 2002/0142083 A1 Oct. 3, 2002

Related U.S. Application Data

(60) Provisional application No. 60/256,487, filed on Dec. 20, 2000, and provisional application No. 60/309,171, filed on Aug. 2, 2001.

(51) Int. Cl.$^7$ ............................................. A23D 7/005
(52) U.S. Cl. ...................... 426/494; 426/601; 424/439; 424/725; 549/413; 203/43; 203/74; 203/80; 203/81
(58) Field of Search ................................ 426/492–494, 426/601; 424/725, 439; 203/43, 74, 80, 81

(56) References Cited

U.S. PATENT DOCUMENTS

| | | | |
|---|---|---|---|
| 4,480,108 A | 10/1984 | Foster | |
| 4,603,142 A | 7/1986 | Burger et al. | 514/456 |
| 5,190,618 A | * 3/1993 | Top et al. | 203/34 |
| 5,487,817 A | 1/1996 | Fizet | |
| 5,504,220 A | 4/1996 | Kuo et al. | |
| 5,512,691 A | 4/1996 | Barnicki et al. | |
| 5,660,692 A | * 8/1997 | Nesburn et al. | 204/157.68 |
| 5,670,669 A | 9/1997 | Hunt | |
| 5,786,491 A | 7/1998 | Hamlin et al. | |
| 5,932,261 A | 8/1999 | Unnithan | |
| 6,159,347 A | 12/2000 | Sumner, Jr. et al. | |
| 6,177,114 B1 | * 1/2001 | Unnithan | 426/417 |
| 6,197,357 B1 | 3/2001 | Lawton et al. | |
| 6,204,290 B1 | 3/2001 | Lane et al. | |
| 6,224,717 B1 | 5/2001 | Sumner, Jr. et al. | |
| 6,350,453 B1 | * 2/2002 | Tan et al. | 424/776 |
| 6,706,898 B2 | * 3/2004 | Sumner, Jr. | 549/413 |
| 2002/0042527 A1 | 4/2002 | Summer, Jr. | |

FOREIGN PATENT DOCUMENTS

| | | |
|---|---|---|
| EP | 0 333 472 A2 | 9/1989 |
| JP | 06 193178 | 7/1994 |
| WO | WO 97/07113 | 2/1997 |
| WO | WO 98/24779 | 6/1998 |
| WO | WO 00/43095 A2 | 7/2000 |
| WO | WO 00/43095 A3 | 9/2000 |
| WO | WO 00/71531 A1 | 11/2000 |

OTHER PUBLICATIONS

Diplock, A.T., et al., "Relationship of Tocopherol Structure to Biological Activity, Tissue Uptake, and Prostaglandin Biosynthesis," *Ann. N.Y. Acad. Sci.* 570:72–84, The New York Academy of Sciences (1989).

(List continued on next page.)

*Primary Examiner*—Carolyn Paden
(74) *Attorney, Agent, or Firm*—Kirkpatrick & Lockhart LLP

(57) ABSTRACT

This invention relates to processes for the production of tocotrienol compounds from biological sources such as palm oil, cereals, grains, and grain oils. The tocotrienol products are recovered in high yields. These tocotrienols are useful as pharmaceuticals, in foodstuffs and as dietary supplements. These compositions are hypocholesterolemic, antioxidizing, antithrombotic, antiatherogenic, antiinflammatory and immunoregulatory in nature. Tocotrienols are known to lower the levels of low density lipoproteins in the bloodstream.

26 Claims, 3 Drawing Sheets

OTHER PUBLICATIONS

Fukuzawa, K., et al., "Increased Platelet–Activating Factor (PAF) Synthesis in Polymorphonuclear Leukocytes of Vitamin E–Deficient Rats," *Ann. N.Y. Acad. Sci. 570*:449–454, The New York Academy of Sciences (1989).

Kritchevsky, D. and Story, J.A., "Fiber, Hypercholesteremia, and Atherosclerosis," *Lipids 13*:366–369, American Oil Chemists' Society (1978).

Niki, E., et al., "Inhibition of Oxidation of Biomembranes by Tocopherol," *Ann. N.Y. Acad. Sci. 570*:23–31, The New York Academy of Sciences (1989).

Qureshi, A.A., et al., "Dietary tocotrienols reduce concentrations of plasma cholesterol, apolipoprotein B, thromboxane $B_2$, and platelet factor 4 in pigs with inherited hyperlipidemias," *Am. J. Clin. Nutr. 53*:1042S–1046S, American Society for Clinical Nutrition (1991).

Qureshi, A.A., et al., "Lowering of serum cholesterol in hypercholesterolemic humans by tocotrienols (palmvitee)," *Am. J. Clin. Nutr. 53*:1021S–1026S, American Society for Clinical Nutrition (1991).

Qureshi, A.A., et al., "The Structure of an Inhibitor of Cholesterol Biosynthesis Isolated from Barley," *J. Biol. Chem. 261*:10544–10550, The American Society of Biological Chemists, Inc. (1986).

Qureshi, A.A., et al., "Suppression of Cholesterogenesis by Plant Constituents: Review of Wisconsin Contributions to NC–167," *Lipids 20*:817–824, American Oil Chemists' Society (1985).

Serbinova, E., et al., "Free Radical Recycling and Intramembrane Mobility in the Antioxidant Properties of Alpha–tocopherol and Alpha–tocotrienol," *Free Radic. Biol. Med. 10*:263–275, Pergamon Press (1991).

Skinner, W.A. and Parkhurst, R. M., "Antioxidant Properties of α–Tocopherol Derivatives and Relationship of Antioxidant Activity to Biological Activity," *Lipids 5*:184–186, American Oil Chemists' Society (1970).

Tan, D.T.S., et al., "Effect of palm–oil–vitamin E concentrate on the serum and lipoprotein lipids in humans," *Am. J. Clin. Nutr. 53*:1027S–1030S, American Society for Clinical Nutrition (1991).

Pending Non–Provisional U.S. Appl. No. 10/246,760, Bartok et al., filed Sep. 19, 2002 (Not Published).

Pending Non–Provisional U.S. Appl. No. 10/285,700, Binder et al., filed Nov. 1, 2002 (Not Published).

International Search Report for International Application No. PCT/US 01/48624, mailed Jul. 10, 2002.

Kato, A., et al., "Separation of tocotrienols," *Chemical Abstracts 105*:775, Abstract No. 105:172787q, American Chemical Society (1986).

* cited by examiner

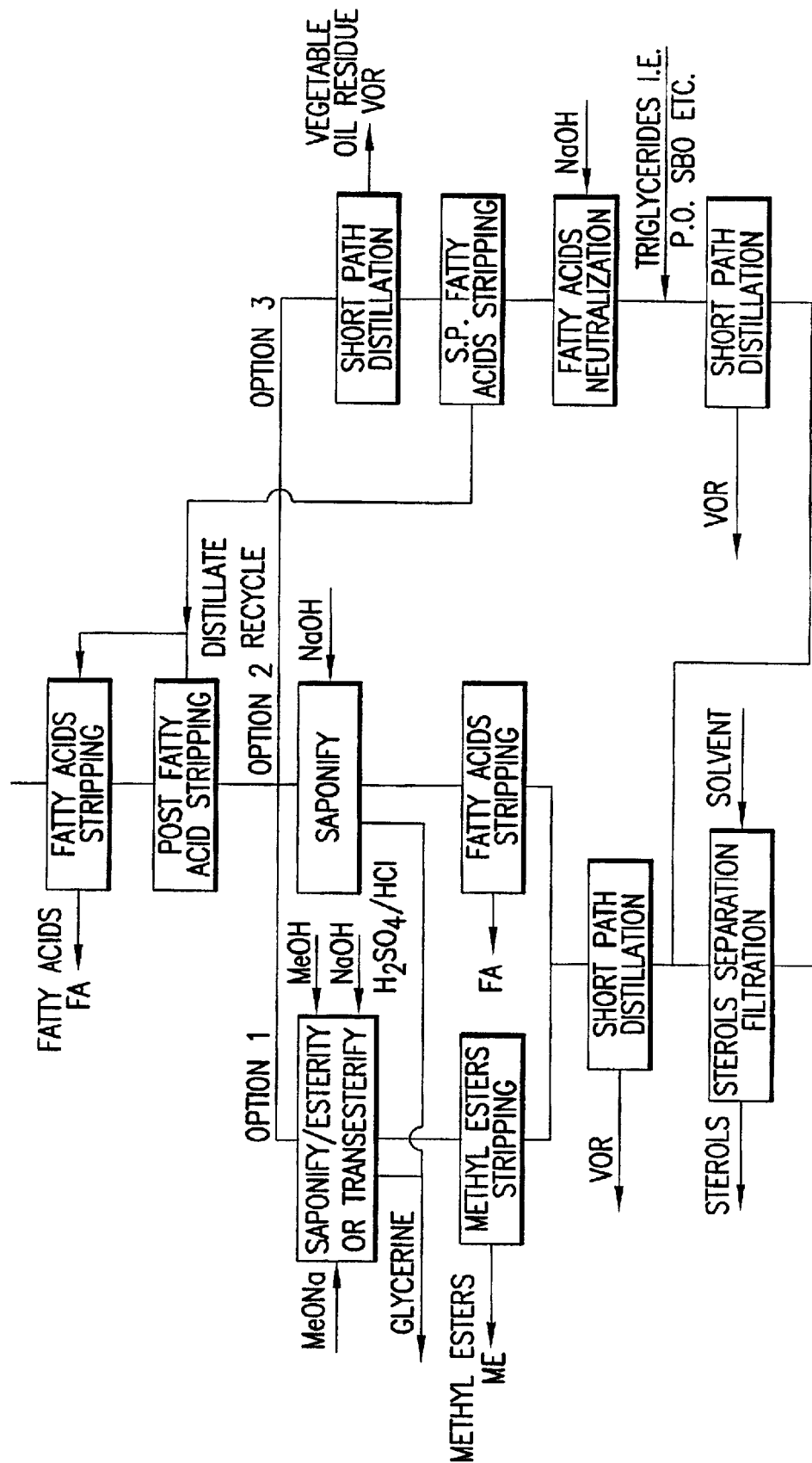

PROCESS FOR THE PRODUCTION OF TOCOTRIENOLS

CROSS-REFERENCE TO RELATED APPLICATIONS

This application claims priority to U.S. Provisional Application Ser. No. 60/256,487, filed Dec. 20, 2000 and to U.S. Provisional Application Ser. No. 60/309,171, filed Aug. 2, 2001.

BACKGROUND OF THE INVENTION

1. Field of the Invention

This invention relates to processes for the production of tocotrienol compounds from biological sources such as palm oil, cereals, grains, and grain oils. The tocotrienol products are recovered in high yields. Tocotrienols are useful as pharmaceuticals, in foodstuffs and as dietary supplements. These compositions are hypocholesterolemic, antioxidizing, antithrombotic, antiatherogenic, anti-inflammatory and immunoregulatory in nature. Tocotrienols are known to lower the levels of low density lipoproteins in the bloodstream.

2. Background Art

Tocopherols and tocotrienols (hereinafter "tocols") are organic compounds that are found in plant material. These compounds are important because they retard the oxidation and spoilage of plant matter. Tocols are also components of vitamin E and possess similar general structural features. Tocols generally have an aromatic chromanol head and a 16-carbon hydrocarbon tail. The number and position of methyl substituents in the chromanol nucleus gives rise to the α-, β-, γ- and δ- homologues. The saturation of the hydrocarbon chain differentiates tocopherols with a saturated chain from tocotrienols with an unsaturated chain as forms of vitamin E. It has also become known that tocols have hypocholesterolemic effects, an important health benefit.

Plant constituents have been proven useful in the prevention and treatment of a wide variety of diseases and conditions. For example, barley has been shown to be particularly effective in lowering lipid levels in animal models (Qureshi et al., "Suppression of Cholesterogenesis by Plant Constituents", Lipids, Vol.20, pp. 817–824 (1985)). More specifically, α-tocotrienol has been identified as a therapeutic agent for hypercholesterolemia (Qureshi et al., "The Structure of an Inhibitor of Cholesterol Biosynthesis Isolated from Barley", J. Biol. Chem., Vol. 261, pp. 10544–10550 (1986)).

High serum cholesterol levels are implicated in numerous diseases and disorders including arteriosclerosis, atherosclerosis, cardiovascular diseases, diabetes mellitus, familial hypercholesterolemia, anorexia nervosa, cirrhosis of the liver, hepatitis and obstructive jaundice. A decrease in low density lipoproteins (LDLs) and/or an increase in the ratio of high density lipoproteins (HDLs) to LDLs will lower the risk of heart disease and retard the progression of the abovementioned diseases and disorders.

It has been found that populations that consume a diet high in certain types of plants, such as cereals and other grains tend to have a low incidence of heart disease and related disorders. This phenomenon was originally attributable to the high fiber content of cereal grains. (Kritchevsky et al., "Fiber, Hypercholesterolemia and Atherosclerosis", Lipids, Vol.13, pp.366–369 (1978)). However, it has also been found that there are several natural plant components that contribute heavily to the low level of cholesterol and diseases related to hypercholesterolemia. Recently, the hypocholesterolemic effects of cereal grains, which contain tocotrienols ("$T_3$") and structurally similar compounds, such as tocopherol ("T"), have been noted.

Tocopherols and tocotrienols are two classes of compounds that are known to have a beneficial effect on the level of cholesterol in the bloodstream. They are found primarily in plant material. For example, high levels of tocols are found in crude vegetable oils such as soybean, barley, sunflower, canola, rapeseed, cottonseed, safflower, corn, palm, palm kernel, and rice bran oils. Rice bran and palm oils have particularly high levels of tocotrienols and tocopherols. Typically, palm oil has about 600–700 mg/kg tocols, with about 50% of the total being tocotrienols. Rice bran oil has about 800–900 mg/kg tocols, with about 57% being in the form of tocotrienols.

As a class, the tocopherols, including d-α-tocopherol (vitamin E), have been extensively studied. As a result of these studies, certain biological activities have been attributed to tocopherols. Such activities include platelet aggregation, and antioxidant functions (Niki et al., "Inhibition of Oxidation of Biomembranes by Tocopherol", Ann. N.Y. Acad. Sci., Vol. 570, pp. 23–31 (1989) and Fukuzawa et al., "Increased Platelet-Activating Factor (PAF) Synthesis in Polymorphonuclear Leukocytes of Vitamin E-Deficient Rats", Ann. N.Y. Acad. Sci., Vol. 570, pp. 449–453 (1989)). Although the exact structure-function relationship is not known, several experiments have highlighted the importance of the phytyl side chain in the biological activity of tocopherols (Skinner et al., "Antioxidant Properties of α-Tocopherol Derivatives and Relationships of Antioxidant Activity to Biological Activity", Lipids, Vol. 5, pp. 184–186 (1969) and Diplock et al., "Relationship of Tocopherol Structure to Biological Activity, Tissue Uptake, and Prostaglandin Biosynthesis", Ann. N.Y. Acad. Sci., Vol. 570, pp. 73–84 (1989)).

In contrast to the tocopherols, interest in the tocotrienols has been limited, as those compounds were not typically considered to be biologically useful. Recently, however, studies have indicated that tocotrienols may be biologically active. For example, U.S. Pat. No. 4,603,142 identifies d-α-tocotrienol, isolated from barley extracts, as an inhibitor of cholesterol biosynthesis (Qureshi, 1986, supra). Various human and animal studies have confirmed the impact of pure tocotrienols, isolated from barley, oats and palm oil, on cholesterol biosynthesis, specifically LDL-cholesterol (Qureshi et al., "Dietary Tocotrienols Reduce Concentrations of Plasma Cholesterol, Apolipoprotein B, Thromboxane $B_2$ and Platelet Factor 4 in Pigs with Inherited Hyperlipidemias", Am J. Clin. Nutr., Vol. 53, pp. 1042S–1046S (1991); Qureshi et al., "Lowering of Serum Cholesterol in Hypercholesterolemic Humans by Tocotrienols (Palmvitee)", Am J. Clin. Nutr., Vol. 53, pp. 1021S–1026S (1991); Tan et al., "The Effect of Palm Oil Vitamin E Concentrate on the Serum and Lipoprotein Lipids in Humans", Am J. Clin. Nutr., Vol. 53, pp. 1027S–1030S (1991)). In addition, γ- and δ-tocotrienols have been indicated for use in the treatment of hypercholesterolemia, hyperlipidemia and thromboembolic disorders (European Patent Application No. 412 419).

The known naturally occurring tocotrienols have been designated α-, β-, γ-, and δ-tocotrienol. These compounds exhibit varying degrees of hypercholesteroemic activity and have also been used as antithrombotic agents and antioxidants. α-$T_3$, for example, displays antioxidant activity against lipid peroxidation in rat liver microsomal membranes and against oxidative damage of cytochrom P-450 (Serbinova, *"Free Radical Biology and Medicine"* (1991)).

During the process of refining vegetable oils, tocopherols and tocotrienols are generally lost as by-products and waste streams. Tocopherols are found at a level of about 1% to about 20%, and tocotrienols are found at about 0.1% to about 5.0%, in deodorizer distillates, steam refining distillates and articulated soapstocks. These by-products and waste streams, however, also contain many other components. Efforts to isolate tocopherols and tocotrienols in high yields have been unsuccessful. Accordingly, a process for the purification of tocopherols and/or tocotrienols from by-products, waste streams, distillates and soapstocks is desirable. The purified tocols, in particular, tocotrienols, can then be used as pharmaceuticals, in foodstuffs and as dietary supplements.

BRIEF SUMMARY OF THE INVENTION

It is a general object of the invention to provide a process for the production of tocotrienols. It is a specific object of the invention to provide a process for the production of tocotrienols comprising:

a) providing a fatty acid distillate (FAD) containing tocotrienols;

b) stripping fatty acids from said FAD at a temperature of about 170° C. to about 255° C. and a pressure of about 0.1 to about 2.0 Torr;

c) distilling the stripped FAD at a temperature of about 150° to about 250° C. and a pressure of about 0.005 to about 0.100 Torr; and d) recovering the tocotrienols.

It is a further object of the invention to provide a tocotrienol product produced by the methods described herein.

It is another specific object of the invention to provide a method for the production of these compounds for use as pharmaceuticals, foodstuffs, and dietary supplements.

Further objects and advantages of the present invention will be clear from the description that follows.

BRIEF DESCRIPTION OF THE FIGURES

FIG. 2a and FIG. 2b are a more detailed schematic for the production of tocotrienols that contains shows several optional pathways.

DETAILED DESCRIPTION OF THE INVENTION

Figure 1:
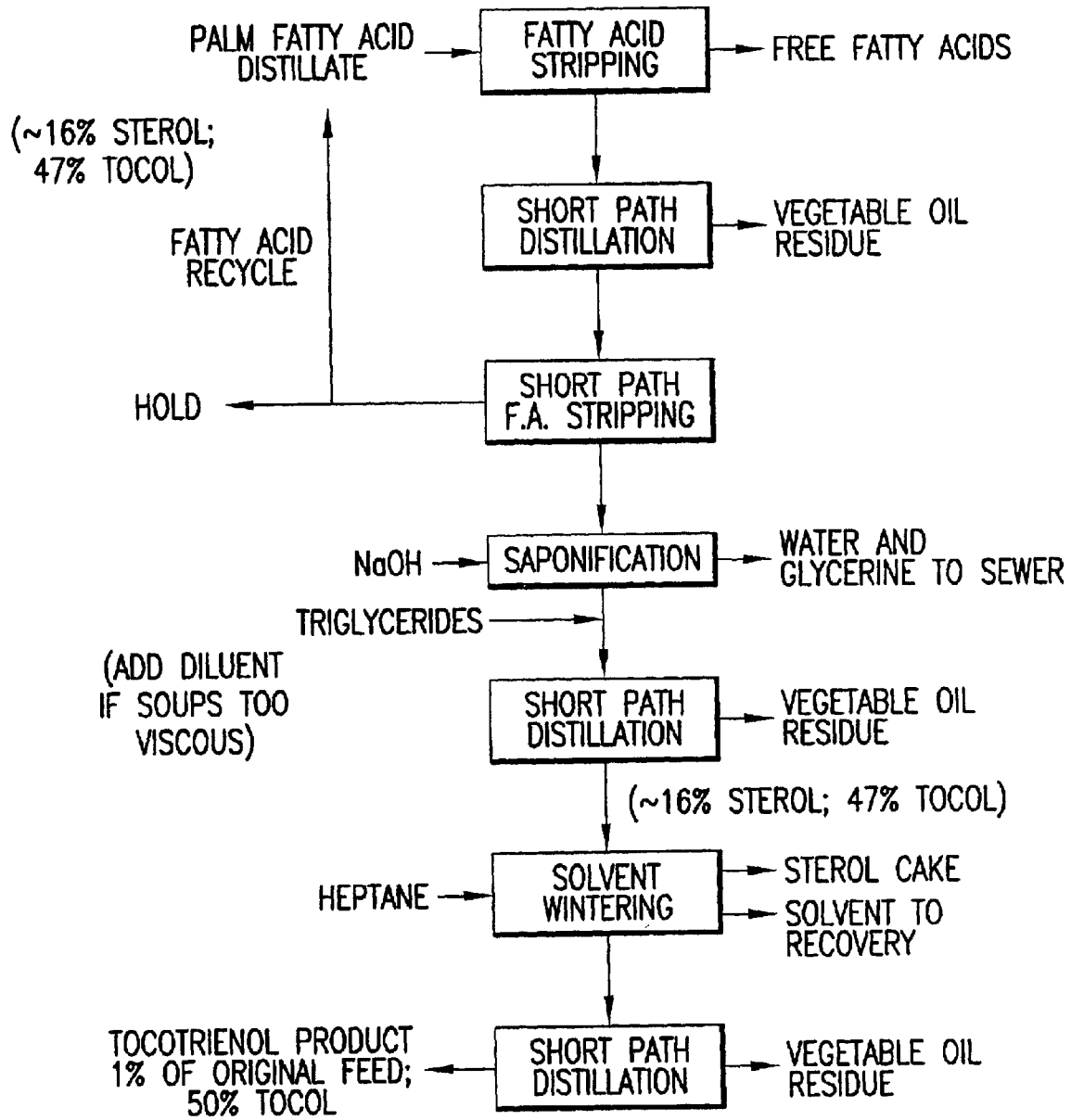
FIG. 1 shows a schematic outlining one process by which the desired tocotrienols are produced from palm fatty acid distillate.
Figure 2B:
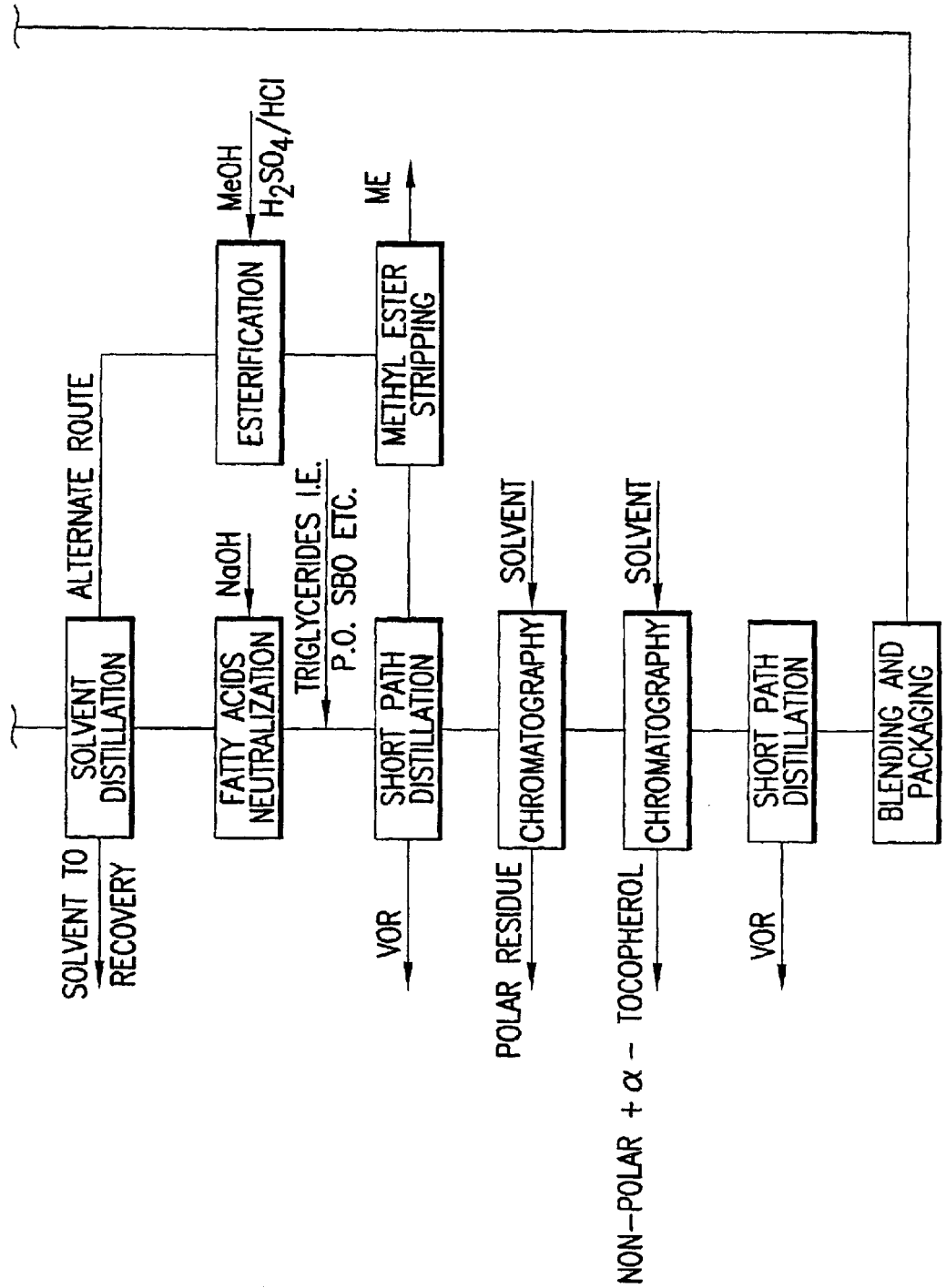

The present invention provides a process by which tocotrienols are extracted from a biomaterial with a high yield. One embodiment of the invention is a process for the production of tocotrienols from a fatty acid distillate comprising the steps of a) providing a fatty acid distillate (FAD) containing tocotrienols; b) stripping fatty acids from said FAD to form a first stripped product; c) short path distillation of said first stripped product to form a first distillate; and d) recovering the tocotrienols. The fatty acid distillate is selected from the group consisting of palm, rice bran, barley, soybean, sunflower, canola, rapeseed, cottonseed, safflower, corn, and palm kernel fatty acid distillates. Preferably the fatty acid distillate is palm fatty acid distillate.

Another embodiment of the invention is a process for the production of tocotrienols comprising a) providing a fatty acid distillate (FAD) containing tocotrienols; b) stripping fatty acids from said FAD at a temperature of about 170° C. to about 255° C., preferably a temperature of about 180° to about 240° C., and a pressure of about 0.1 to about 2.0 Torr, preferably a pressure of about 0.5 to about 1.5 Torr; c) distilling the stripped FAD at a temperature of about 150° to about 250° C., preferably a temperature of about 180° C. to about 210° C., and a pressure of about 0.005 to about 0.100 Torr, preferably a pressure of about 0.010 to about 0.050 Torr; and d) recovering the tocotrienols. The fatty acid distillate can be selected from the group consisting of palm, rice bran, barley, soybean, sunflower, canola, rapeseed, cottonseed, safflower, corn, and palm kernel fatty acid distillates. Preferably, the fatty acid distillate is palm fatty acid distillate.

Another embodiment of the invention is a process that comprises the following steps between steps c) and d) as described supra:

i) subjecting the first short path distillate to a second fatty acid stripping at a temperature of between about 120° C. and about 180° C. and an absolute pressure of about 0.01 Torr and about 0.5 Torr;

ii) saponifying the stripped product at a temperature of about 100° C. to about 120° C. and an absolute pressure of about 15 to about 20 PSIG;

iii) distilling the saponified product at a temperature of about 150° to about 250° C. and a pressure of about 0.005 to about 0.100 Torr;

iv) solvent wintering the distillate of (iii) at a temperature of between 0° C. and −15° C.;

v) distilling the product of (iv) at a temperature of about 150° C. to about 250° C. and a pressure of about 0.005 to about 0.100 Torr.

Another embodiment of the process comprises the steps of a) providing a palm fatty acid distillate (PFAD) containing tocotrienols; b) stripping fatty acids from said PFAD to form a first stripped product; c) short path distillation of said first stripped product to form a first distillate; d) short path stripping the fatty acids from the first distillate to form a second stripped product; e) saponifying said second stripped product to form a saponified product; f) a second short path distillation of said saponified product to form a second distillate; g) solvent wintering (via filtration) of the second distillate to form a stripped filtrate; h) a third short path distillation of said stripped filtrate; and i) recovering the tocotrienols. Optionally, the process comprises additional saponification and stripping steps. The process further optionally comprises neutralization of fatty acids and chromatography steps.

One embodiment of the present invention comprises a process for extracting tocotrienols from palm fatty acid distillate (PFAD). PFAD has the following composition, in approximate amounts:

| | |
|---|---|
| Total tocols: | 1.0% |
| Free fatty acids: | 40.0% |
| Sterols: | 0.3% |
| Steryl esters: | 0.5% |
| Triglycerides: | 28.5% |
| Diglycerides: | 13.2% |
| Monoglycerides: | 10.5% |
| Unsaponifiables (Others): | 6.0% |

The process itself comprises the numerous steps as described herein.

The FAD feed material is fed to a flash evaporator equipped with a properly sized pre-heater, flash chamber with mist eliminator, secondary evaporator, a stripping section and an internal condenser with cold trap. Vacuum may be generated by any known vacuum generating device in any combination deemed desirable. The stripping conditions are a temperature of between about 170° C. and about 255° C., preferably between about 180° C. and about 240° C. and an absolute pressure of between about 0.1 Torr and about 2.0 Torr, preferably about 0.5 Torr to about 1.5 Torr. The feed rate to yield residence time is between about 0.25 minutes and about 30 minutes, preferably from about 0.5 minutes to about 1.5 minutes.

The second step of the tocotrienol purification process is a short path distillation step. The stripped residue from the previous step is subjected to short path distillation utilizing state-of-the-art short path distillation equipment. The distillation conditions are a temperature between about 150° C. and 250° C., preferably between about 180° C. and about 210° C., and an absolute pressure between about 0.005 and about 0.1 Torr, preferably from about 0.01 Torr to about 0.05 Torr. The typical residence time in short path distillation units is between about 1.0 second and about 30 seconds.

The distillate from the previous step is then subjected to a second short path stripping procedure in order to remove any remaining fatty acids from the first fatty acid stripping step. This is a much more aggressive stripping procedure that also will remove approximately 27% of the available tocols in addition to the fatty acids. For this reason, this cut is recycled back into the first fatty acids stripping step for re-processing. The residue, approximately 12% of the original feed and containing approximately 5.1% tocols, is collected in a vessel that is suitable for subsequent processing. The short path stripping conditions are a temperature between about 120° and 180° C., preferably between about 140° C. to about 160° C., and an absolute pressure of about 0.01 Torr to about 0.5 Torr, preferably from about 0.03 Torr to about 0.08 Torr.

The resulting product is then subjected to saponification. The stripped residue from the previous step is saponified neat, using either 50% NaOH or KOH in water as a caustic material. The reactor for this step is stainless steel or glass lined and must be equipped with adequate agitation and optional heating and cooling apparatus. The vessel must be rated for at least 25 PSIG internal pressure and equipped with the necessary protective devices. A condenser with cooling and vacuum and a vacuum receiver must be available for degassing purposes. The saponification step is performed in order to saponify the esters and convert them into their respective alcohols and fatty acids salts. Further, the higher molecular weight fatty acids that survived the previous stripping steps must also be saponified. Once the saponification is complete, the excess water and glycerine is decanted and sewered. The product, approximately 11.0% of the original feed, contains the generated soaps and is held for the next purification step. The reaction conditions for the saponification are a temperature between about 100° C. and 120° C., preferably about 110° C., and an absolute pressure of about 15–20 PSIG. The reaction time is about two hours after the addition of the caustic material. The reaction mixture must be agitated continuously from the addition of the caustic material, and throughout the reaction. After decanting, the degassing takes place, first at about 100° C. at atmospheric pressure, and as the temperature rises over 100° C., the reactor is placed under vacuum at a pressure of about 25 in Hg. The temperature is allowed to rise to about 120° C. to about 130° C. After degassing, the saponified product is held for the subsequent step.

The saponified product is subjected to a second short path distillation. At this point, it may be necessary to add about 10% to about 20% triglycerides in order to solubilize the soaps generated during the previous step. The saponified and stripped product from the previous step, either with or without the added triglycerides, is subjected to another distillation. The conditions for distillation are a temperature of about 150° C. to about 250° C., preferably about 180° C. to about 210° C., and an absolute pressure of about 0.005 Torr to about 0.1 Torr, preferably about 0.01 Torr to about 0.05 Torr. The residue generated by the distillation contains little or no tocols, and is stored as a vegetable oil residue. The distillate, which is about 1.5% of the original feed, contains about 40% tocols and is held for the subsequent step.

The distillate is now subjected to solvent wintering, or the removal of sterols from the preparation. The distillate contains approximately 16% sterols for removal. The distillate is dissolved in heptane, chilled and filtered on a suitable filtration unit. Alternatively, other solvents may be used, including, but not limited to, ethanol, methanol, acetone and aqueous solutions thereof. The filtration unit may be a rotary vacuum filter, a deep bed filter, a sparkler filter, a nutsch filter, a filter press, or any other suitable filter. The filtering conditions are a temperature between about 0° C. and about −15° C., preferably between about −5° C. to about −10° C. A filter aid may be used to increase the speed of filtration. The type of filter aid is dependent upon the type of filter employed. The resulting filter cake, which contains primarily sterols, is desolventized and combined with phytosterols produced in other vitamin E production processes, or is discarded into the vegetable oil residue. The filtrate is desolventized by distillation followed by vacuum stripping. The stripped filtrate contains approximately 47% tocols and about 1% sterols.

The stripped filtrate from the previous step is subjected to a third short path distillation at a temperature of about 150° C. to about 250° C., preferably about 180° C. to about 210° C. and an absolute pressure of about 0.005 Torr to about 0.1 Torr, preferably about 0.01 Torr to about 0.05 Torr. The resulting final tocotrienol product, about 0.5% to about 5%, preferably about 1% of the original feed, contains from about 40% to about 60%, preferably about 50% tocols, from about 0.5% to about 5% sterols, preferably about 1% sterols, and from about 35% to about 59.5%, preferably about 49% other unsaponifiables and unknowns. Additionally, the final product contains from about 15% to about 30% tocopherols.

The final product contains α-, β-, γ- and δ-tocotrienols. Additionally, further purification steps can be employed to separate the tocotrienols from one another, resulting in a single tocotrienol isomer preparation. These tocotrienols, either as a mixture or as separate isomers, are used as pharmaceuticals, foodstuffs or dietary supplements. The amount of total tocotrienols in the final product ranges from about 295 mg/g to about 410 mg/g, preferably from about 331 mg/g to about 382 mg/g. The individual tocotrienols are present in the following concentrations: α- tocotrienol is present in an amount ranging from about 140 mg/g to about 165 mg/g, preferably about 150 mg/g to about 160 mg/g. β-tocotrienol ranges from about 5 mg/g to about 15 mg/g, preferably from about 10 mg/g to about 14 mg/g. γ-tocotrienol is present in the final product in an amount ranging from 120 mg/g to about 170 mg/g, preferably from about 130 mg/g to about 160 mg/g. δ-tocotrienol is present in an amount ranging from about 30 mg/g to about 60 mg/g, preferably from about 41 mg/g to about 48 mg/g. Other compounds will also be found in the final isolation product. For example, sterols will be present in an amount ranging from about 3% to about 15%, preferably about 4% to about 9%.

Other steps may be incorporated into the tocotrienol production process. For example, additional saponification, stripping steps, neutralization of fatty acids and chromatography steps may be incorporated prior to the final short path distillation. These steps would further increase the purity of the final tocotrienol product. Further, the tocol containing material may be concentrated between steps, resulting in an improved tocol yield. In addition, the different tocotrienol homologues may be individually isolated, so that pharmaceuticals, dietary supplements and foodstuffs may be formulated with any one of the tocotrienol homologues, or a mixture thereof.

EXAMPLES

Example 1

Tocotrienols and tocopherols were isolated from palm fatty acid distillate by the protocol as described below.

A fatty acid distillate (FAD) containing tocotrienols was provided and the fatty acids stripped from the FAD at a temperature of about 180° to about 240° C. and a pressure of about 0.5 to about 1.5 Torr. The stripped FAD was distilled at a temperature of about 180° C. to about 210° C. and a pressure of about 0.010 to about 0.050 Torr. The product was then subjected to a second fatty acid stripping at a temperature of between about 120° C. and about 180° C. and an absolute pressure of about 0.01 Torr and about 0.5 Torr; saponified at a temperature of 100° C. to about 120° C. and an absolute pressure of about 15 to about 20 PSIG. The saponified product was redistilled at a temperature of about 150° to about 250° C. and a pressure of about 0.005 to about 0.100 Torr and solvent wintered at a temperature of about 0° C. and about −15° C. This product was redistilled at a temperature of about 150° to about 250° C. and a pressure of about 0.005 to about 0.100 Torr, and the tocotrienols recovered.

The isolated material had the profile shown in Table 1 below.

TABLE 1

|  | Intermediate Product | ADM 57 (Final Product) |
| --- | --- | --- |
| Tocopherols |  |  |
| alpha, mg/g | 168.4 | 200.4 |
| beta, mg/g | 1.3 | 1.3 |
| gamma, mg/g | 10.5 | 3.2 |
| delta, mg/g | 3.7 | 2.0 |
| total, mg/g | 183.9 | 206.9 |
| Tocotrienols |  |  |
| alpha, mg/g | 156.5 | 154.4 |
| beta, mg/g | 11.8 | 12.8 |
| gamma, mg/g | 159.4 | 138.8 |
| delta, mg/g | 42.9 | 47.1 |
| total, mg/g | 370.6 | 353.1 |
| Total Tocols, mg/g | 554.5 | 560.0 |
| Acid Value | 12.7 | 2.5 |
| Peroxide Value | 0.3 | 1.4 |
| Saponification # | 49.4 | 38.0 |
| Gardner | 13.8 | 14.5 |
| Total Sterols, % | 7.6 | 5.0 |
| % T3 | 37.06 | 35.31 |
| % T | 18.39 | 20.69 |
| Total Tocols, mg/g | 554.50 | 560.00 |
| % Total Tocols | 55.45 | 56.00 |
| % T3 of Total Tocols | 66.83 | 63.05 |
| % T of Total Tocols | 33.17 | 36.95 |
| T3/T | 2.02 | 1.71 |

TABLE 1-continued

|  | Intermediate Product | ADM 57 (Final Product) |
| --- | --- | --- |
| γ-T3/α-T3 | 1.02 | 0.90 |
| α-T/α-T + γ-T3 | 0.53 | 0.68 |
| γ-T/α-T | 0.06 | 0.02 |
| T3/Str | 4.88 | 7.06 |

Having now fully described the present invention in some detail by way of illustration and example for purposes of clarity of understanding, it will be obvious to one of ordinary skill in the art that the same can be performed by modifying or changing the invention with a wide and equivalent range of conditions, formulations and other parameters thereof, and that such modifications or changes are intended to be encompassed withing the scope of the appended claims.

All publications, patents and patent applications mentioned in this specification are indicative of the level of skill of those skilled in the art to which this invention pertains, and are herein incorporated by reference to the same extent as if each individual publication, patent or patent application was specifically and individually indicated to be incorporated by reference.

What is claimed is:

1. A process for the production of tocotrienols comprising:
    a) providing a fatty acid distillate (FAD) containing tocotrienols;
    b) stripping fatty acids from said FAD at a temperature of about 170° C. to about 255° C. and a pressure of about 0.1 to about 2.0 Torr;
    c) distilling the stripped FAD at a temperature of about 150° to about 250° C. and a pressure of about 0.005 to about 0.100 Torr; and
    d) recovering the tocotrienols, wherein said tocotrienol product comprises α-, β-, γ, and δ-tocotrienols in an amount ranging from about 295 mg/g to about 410 mg/g.

2. The process of claim 1, wherein said FAD is selected from the group consisting of palm, rice bran, barley, soybean, sunflower, canola, rapeseed, cottonseed, safflower, corn, and palm kernel fatty acid distillates.

3. The process of claim 2, wherein said FAD is palm fatty acid distillate.

4. The process according to claim 1, wherein (b) is performed at a temperature of about 180° to about 240° C. and a pressure of about 0.5 to about 1.5 Torr and (c) is performed at a temperature of about 180° C. to about 210° C. and a pressure of about 0.010 to about 0.050 Torr.

5. The process according to claim 1 further comprising the following steps subsequent to step c) and prior to step d) of claim 1:
    a) subjecting a first short path distillate to a second fatty acid stripping at a temperature of between about 120° C. and about 180° C. and an absolute pressure of about 0.01 Torr and about 0.5 Torr;
    b) saponifying the stripped product at a temperature of about 100° C. to about 120° C. and an absolute pressure of about 15 to about 20 PSIG;
    c) distilling the saponified product at a temperature of about 150° to about 250° C. and a pressure of about 0.005 to about 0.100 Torr;
    d) solvent wintering the distillate of (iii) at a temperature of between about 0° C. and about −15° C.;

e) distilling the product of (iv) at a temperature of about 150° to about 250° C. and a pressure of about 0.005 to about 0.100 Torr.

6. The process according to claim 5, wherein said FAD is selected from the group consisting of palm, rice bran, barley, soybean, sunflower, canola, rapeseed, cottonseed, safflower, corn, and palm kernel fatty acid distillates.

7. The process according to claim 6, wherein the FAD is palm fatty acid distillate.

8. The process according to claim 5, wherein b) is performed at a temperature of about 180° to about 240° C. and a pressure of about 0.5 to about 1.5 Torr; c) is performed at a temperature of about 180° C. to about 210° C. and a pressure of about 0.010 to about 0.050 Torr; i) is performed at a temperature of between about 140° C. to about 160° C. and pressure of about 0.03 Torr to about 0.08 Torr; ii) is performed at a temperature of about 110° C. and a pressure of about 15 to about 20 PSIG; iii) is performed at a temperature of about 180° C. to about 210° C. and a pressure of about 0.010 to about 0.050 Torr; iv) is performed at a temperature of about −5° C. to about −10° C.; and v) is performed at a temperature of about 180° C. to about 210° C. and a pressure of about 0.010 to about 0.050 Torr.

9. The process according to claim 8, wherein glycerine and excess water are decanted from the saponified product, which is then subject to degassing.

10. The process according to claim 8, wherein triglycerides are added to the saponified product prior to step iii) at a final concentration of about 10% to about 20%.

11. The process according to claim 8, further comprising the step of chromatographing the distillate from step iii).

12. A tocotrienol product produced by a process, comprising.
  a) providing a fatty acid distillate (FAD) containing tocotrienols;
  b) stripping fatty acids from said FAD at a temperature of about 170° C. to about 255° C. and a pressure of about 0.1 to about 2.0 Torr;
  c) distilling the stripped FAD at a temperature of about 150° to about 250° C. and a pressure of about 0.005 to about 0.100 Torr; and
  d) recovering the tocotrienols;
  wherein said tocotrienol product comprises α-, β-, γ, and δ-tocotrienols in an amount ranging from about 295 mg/g to about 410 mg/g.

13. The tocotrienol product of claim 12, wherein said amount is about 331 mg/g to about 383 mg/g.

14. The tocotrienol product of claim 12, wherein said tocotrienol product comprises α-tocotrienol in an amount ranging from about 140 mg/g to about 165 mg/gm.

15. The tocotrienol product of claim 14, wherein said amount is about 150 mg/g to about 160 mg/g.

16. The tocotrienol product of claim 12, wherein said tocotrienol product comprises β-tocotrienol in an amount ranging from about 5 mg/g to about 15 mg/g.

17. The tocotrienol product of claim 16, wherein said amount is about 10 mg/g to about 14 mg/g.

18. The tocotrienol product of claim 12, wherein said tocotrienol product comprises γ-tocotrienol in an amount ranging from about 120 mg/g to about 170 mg/g.

19. The tocotrienol product of claim 18, wherein said amount is about 130 mg/g to about 160 mg/g.

20. The tocotrienol product of claim 12, wherein said tocotrienol product comprises δ-tocotrienol in an amount ranging from about 30 mg/g to about 60 mg/g.

21. The tocotrienol product of claim 20, wherein said amount is about 41 mg/g to about 48 mg/g.

22. The tocotrienol product of claim 12, further comprising sterols in an amount ranging from about 3% to about 5%.

23. The tocotrienol product of claim 22, wherein said amount is about 4% to about 9%.

24. A pharmaceutical product comprising the tocotrienol product of claim 12.

25. A foodstuff comprising the tocotrienol product of claim 12.

26. A dietary supplement comprising the tocotrienol product of claim 12.

* * * * *